United States Patent
Brieva et al.

[11] Patent Number: 6,103,250
[45] Date of Patent: Aug. 15, 2000

[54] ANHYDROUS COSMETIC COMPOSITIONS CONTAINING EMULSIFYING SILOXANE ELASTOMER

[75] Inventors: Hernando Brieva, Manalapan, N.J.; Geoffrey Robert Hawkins, Langhorne, Pa.; Shaoxiang Lu, Plainsboro; Tian Xiang Wang, Edison, both of N.J.

[73] Assignee: Revlon Consumer Products Corporation, New York, N.Y.

[21] Appl. No.: 09/347,551

[22] Filed: Jul. 6, 1999

[51] Int. Cl.[7] .............................. A61K 7/00; A61K 7/021; A61K 7/025; A61K 7/32; A61K 9/00
[52] U.S. Cl. ............................ 424/401; 424/63; 424/64; 424/65; 424/400; 424/DIG. 5; 514/474
[58] Field of Search ..................................... 424/400, 401, 424/63, 64, 65, DIG. 5; 514/474

[56] References Cited

U.S. PATENT DOCUMENTS

| | | | |
|---|---|---|---|
| 5,266,321 | 11/1993 | Shukuzaki | 424/401 |
| 5,387,417 | 2/1995 | Rentsch | 424/401 |
| 5,412,004 | 5/1995 | Tachibana | 524/27 |
| 5,599,533 | 2/1997 | Stepniewski | 424/78.02 |
| 5,849,314 | 12/1998 | Dobkowski | 424/401 |
| 5,853,741 | 12/1998 | Znaiden et al. | 424/401 |
| 5,919,437 | 7/1999 | Lee | 424/68 |

FOREIGN PATENT DOCUMENTS

| | | |
|---|---|---|
| 790 055 | 8/1997 | European Pat. Off. . |
| 908 175 | 4/1999 | European Pat. Off. . |

*Primary Examiner*—Shelley A. Dodson
*Assistant Examiner*—Marina Lamm
*Attorney, Agent, or Firm*—Julie Blackburn

[57] ABSTRACT

An anhydrous cosmetic composition comprising, by weight of the total composition, 1–50% of a polar, emulsifying siloxane elastomer, 0.01–40% particulate material; and 1–70% of a nonpolar oil; an anhydrous cosmetic composition comprising an emulsifying siloxane elastomer and an incompatible nonaqueous polar ingredient, wherein the emulsifying siloxane elastomer is present in an amount sufficient to render the incompatible nonaqueous polar ingredient compatible in the anhydrous cosmetic composition; and a method for preparing stable, anhydrous cosmetic compositions comprising at least one incompatible nonaqueous polar ingredient, comprising adding to the anhydrous composition an emulsifying siloxane elastomer in an amount sufficient to cause the incompatible nonaqueous polar ingredient to become compatible in the anhydrous cosmetic composition.

15 Claims, No Drawings

ANHYDROUS COSMETIC COMPOSITIONS CONTAINING EMULSIFYING SILOXANE ELASTOMER

TECHNICAL FIELD

The invention is in the field of anhydrous cosmetic compositions such as lipstick, blush, powder, antiperspirant, deodorant, and the like, which contain a silicone elastomer which is a water-in-oil emulsifier.

BACKGROUND OF THE INVENTION

A wide variety of cosmetic compositions are most often found in the anhydrous form, for example, lipstick, eyeshadow, blush, concealer, and so on. Such cosmetics often contain high levels of nonpolar ingredients such as fats, oils, and waxes, which provide the cosmetics with a certain heavy, occlusive, feeling when applied to skin or lips. Anhydrous polar ingredients, for example, mono- and difunctional alcohols like glycerin, propylene glycol, and the like, are known for their ability to improve formula aesthetics and are often used as carriers for skin treatment actives. However, these polar materials cannot be added to anhydrous formulations because they are generally incompatible with the nonpolar ingredients present. In addition, it is desireable to incorporate certain active ingredients such as ascorbic acid into anhydrous skin creams and lotions because ascorbic acid is very unstable in water. The problem, however, is that such anhydrous creams or lotions are not aesthetically pleasing because no water is present.

Silicone elastomers are generally three dimensional cross-linked chain polymers which have rubber-like properties. Silicone elastomers are known for use in both anhydrous and emulsion form cosmetics, and are known to provide unique feel and aesthetics to cosmetic formulas.

U.S. Pat. No. 5,849,314 describes a skin treatment composition containing a nonemulsifying siloxane elastomer. The composition contains 0–5% by weight water.

U.S. Pat. No. 5,833,973 teaches skin treatment compositions in the emulsion form containing a nonemulsifying siloxane elastomer and from 50 to 85% by weight water.

PCT/WO 98/00104 teaches cosmetic powder compositions containing a nonemulsifying siloxane elastomer. The compositions are anhydrous.

U.S. Pat. No. 5,599,533 teaches nonemulsifying silicone elastomers in water in oil emulsion cosmetic compositions.

U.S. Pat. No. 5,412,004 teaches emulsifying siloxane elastomers in water in oil emulsion cosmetic compositions.

None of the above patents describe silicone elastomers containing polar groups, otherwise referred to as emulsifying siloxane elastomers in anhydrous cosmetic compositions. Emulsifying silicone elastomers contain hydrophilic functional groups that provide the elastomer with emulsification properties, in particular, the ability to emulsify water in oil mixtures. Nonemulsifying silicone elastomers do not contain such hydrophilic functional groups and generally are not capable, alone, of emulsifying water and oil mixtures. The use of emulsifying siloxane elastomers, which are designed for emulsification of water in oil emulsion compositions, in anhydrous cosmetic compositions, provides certain unique and desireable properties in anhydrous cosmetic compositions. Certain nonaqueous polar ingredients that improve aesthetics of anhydrous cosmetic compositions can be added to such anhydrous compositions which markedly improve aesthetics. In addition, aesthetically pleasing anhydrous compositions containing water sensitive ingredients such as ascorbic acid can be formulated with ease.

The object of the invention is to provide anhydrous cosmetic compositions with improved aesthetics.

Another object of the invention is to provide stable, anhydrous cosmetic compositions that additionally contain nonaqueous polar ingredients.

Another object of the invention is to provide stable anhydrous cosmetic compositions containing polyols.

Another object of the invention is to provide a stable emulsion systems for the incorporation of skin treatment actives into anhydrous systems.

SUMMARY OF THE INVENTION

The invention comprises an anhydrous cosmetic composition comprising, by weight of the total composition:

0.1–95% of an emulsifying siloxane elastomer, 0.01–40% of particulate material, and 1–70% of a nonpolar phase.

The invention also comprises an anhydrous cosmetic composition comprising an emulsifying siloxane elastomer and an incompatible nonaqueous polar ingredient, wherein the emulsifying siloxane elastomer is present in an amount sufficient to render the incompatible nonaqueous polar ingredient compatible in the anhydrous cosmetic composition.

The invention also comprises a method for preparing stable, anhydrous cosmetic compositions comprising at least one incompatible nonaqueous polar ingredient, comprising adding to the anhydrous composition an emulsifying siloxane elastomer in an amount sufficient to cause the incompatible nonaqueous polar ingredient to become compatible in the anhydrous cosmetic composition.

DETAILED DESCRIPTION

The cosmetic compositions of the invention may be in the form of solids, semi-solids, or liquids at room temperature. The compositions may be in the form of sticks, cakes, liquids, and so on. All percentages mentioned herein are percentages by weight unless otherwise indicated. The term "anhydrous" means that no water is intentionally added to the compositions, however trace amounts of water may be present due to its presence in certain ingredients which are used to formulate the cosmetic compositions.

I. Emulsifying Siloxane Elastomer

The compositions of the invention comprise 0.1–95%, preferably 0.5–50%, more preferably 1–35% by weight of the total composition of an emulsifying siloxane elastomer. The term "emulsifying" means that the siloxane elastomer contains a certain polar, or hydrophilic, functional groups that enable the elastomer to provide emulsification properties when used in water and oil emulsions. The types of hydrophilic groups that may be present on the elastomer include hydroxyl, polyethyleneoxy, polypropyleneoxy, amino, and the like. In addition, the elastomer may be reacted with certain other compounds or molecules such as sugars (sucrose, glucose), sorbitan derivatives (sorbitan sesquioleate, sorbitan stearate), betaines (which are quaternized alkyl or substituted alkyl derivatives of N,N-dimethyl glycine), and the like, which confer polarity. The hydrophilic groups may be found on the silicon backbone or on the cross linking groups of the elastomer. Such elastomers are generally formed by the reaction of a dimethyl, methyl hydrogen siloxane and a divinyl compound. Either one or both of the dimethyl, methylhydrogen siloxane or the divinyl compound may be substituted with one or more hydrophilic functional groups, provided there are sufficient hydrophilic groups present on the resulting elastomer to confer emulsifying properties thereto. For example, the dimethyl, methylhydrogen siloxane may be a linear or crosslinked (i.e. an MQ resin) silicone, and may contain one or more substituted hydrophilic functional groups such as hydroxyl or alkyleneoxy. By alkyleneoxy is meant ethyleneoxy alone or in combination with propyleneoxy. In the case of the latter, the amount of propyleneoxy (which normally confers lipophilic properties) is not present to a degree that causes the resulting elastomer to lose its general hydrophilic character. It is also possible that the dimethyl, methylhydrogen siloxane is not substituted with any hydrophilic functional groups, but rather the divinyl, crosslinking compound contains these radicals. Suitable divinyl compounds include alpha omega dienes, divinyl substituted MQ resins, divinyl subsituted dimethylsiloxanes, and so on. When the hydrophilic groups are subsituted on the divinyl crosslinking compound, the alpha omega diene or divinyl substituted MQ resins will be substituted with one or more of the hydrophilic groups mentioned above. Particularly suitable as the divinyl crosslinking compound containing hydrophilic functional groups are divinyl terminated alkyleneoxy compounds, divinyl substituted dimethicone copolyol, and so on.

Preferred emulsifying siloxane elastomers are gelling agents as set forth in U.S. Pat. No. 5,412,004, which is hereby incorporated by reference. These siloxane elastomers are formed by the addition polymerization of I and II, as defined below:

I. an organohydrogenpolysiloxane as described in A, B, or C wherein:

(A) is $$\frac{R^1_a R^2_b H_c SiO(4-a-b-c)}{2}$$

(1) $R^1$ is a substituted or unsubstituted alkyl, aryl, or aralkyl group having 1–18 carbon atoms, or a halogenated hydrocarbon group; and
(2) $R^2$ is $-C_nH_{2n}O(C_2H_4O)_d(C_3H_6O)_eR_3$
  (a) wherein $R^3$ is a hydrogen, a saturated aliphatic hydrocarbon group having 1–10 carbon atoms, or a group $-(CO)-R^5$
    (i) wherein $R^5$ is a saturated aliphatic hydrocarbon having 1 to 5 carbon atoms,
  (b) d is an integer of 2 to 200,
  (c) e is an integer of 0 to 200, provided that d+e is 3–200; and
  (d) n is 2 to 6;
(3) a is 1 to 2.5;
(4) b is 0.001 to 1.0; and
(5) c is 0.001 to 1.0; or an organohydrogenpolysiloxane having the following formula, (B) is $$\frac{R^1_f H_g SiO(4-f-g)}{2}$$

(1) wherein $R^1$ is the same as defined in formula I(A) above,
(2) f is 1.0 to 3.0;
(3) g is 0.001 to 1.5; and
(C) is a mixture of said organohydrogenpolysiloxanes of formulas I(A) and I(B); and II. a compound as described in A, B, or C wherein:

(A) is $C_mH_{2m-1}O(C_2H_4O)_h(C_3H_6O)_iC_mH_{2m-1}$
(1) wherein h is an integer of 2 to 200,
(2) i is an integer of 0 to 200 provided that h+i is 3 to 200; and
(3) m is 2 to 6;
(B) is $$\frac{R^1_j R^4_k SiO(4-j-k)}{2}$$

(1) wherein $R^1$ is the same as defined in formula I(A) above,
(2) $R^4$ is a monovalent hydrocarbon group having an aliphatic unsaturated bond at the terminal thereof and containing 2 to 10 carbon atoms;
(3) j is 1.023 to 3.0; and
(4) k is 0.001 to 1.5;
(C) is a mixture of the polyoxyalkylene of II(A) and the organopolysiloxane of II(B), wherein at least one organohydrogenpolysiloxane of formulas I or at least one polyoxyalkylene of formulas II is contained as an essential component of the addition polymerization.

Preferably I is:

(A)

$$\frac{R^1_a R^2_b H_c SiO(4-a-b-c)}{2}$$

(1) wherein $R^1$ is a substituted or unsubstituted alkyl group having 1–18 carbon atoms; and
(2) $R^2$ is $-C_nH_{2n}O(C_2H_4O)_d(C_3H_6O)_eR_3$
  (a) wherein $R^3$ is a hydrogen, a saturated aliphatic hydrocarbon group having 1–10 carbon atoms, or a group $-(CO)-R^5$
    (i) wherein $R^5$ is a saturated aliphatic hydrocarbon having 1 to 5 carbon atoms,
  (b) d is an integer of 2 to 200,
  (c) e is an integer of 0 to 200, provided that d+e is 3–200; and
  (d) n is 2 to 6;
(3) a is 1 to 2.5;
(4) b is 0.001 to 1.0; and
(5) c is 0.001 to 1.0.

and II is:

(A) $C_mH_{2m-1}O(C_2H_4O)_h(C_3H_6O)_iC_mH_{2m-1}$
(1) wherein h is an integer of 2 to 200,
(2) i is an integer of 0 to 200 provided that h+i is 3 to 200; and
(3) m is 2 to 6;

Particularly preferred is an emulsifying siloxane elastomer sold by Shin-Etsu Silicones of America under the tradename KSG21 which is a colorless translucent paste comprised of, by weight of the paste, about 25–35% siloxane elastomer and 65–75% dimethicone. KSG21 comprises a silicon backbone cross-linked with polyether segments.

II. The Particulate Material

The compositions of the invention further comprise 0.01–80%, preferably 0.05–75%, more preferably 1–70% by weight of the total composition of particulate material. The particulate material may be comprised of pigments either alone or in combination with particulate fillers (together referred to as "particulate material"). Additionally, in the case where the claimed compositions are antiperspirants, the particulate material may comprise antiperspirant salts either alone or in combination with particulate fillers. Preferably, the particulate matter has a particle size of 0.02 to 100, preferably 0.5 to 100, microns.

A. Pigments and Particulate Fillers

In the case where the particulate matter comprises pigments and/or particulate fillers, the particulate matter may be colored or non-colored (non-colored meaning without color or white in color). Suitable particulate fillers include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silk powder, silica, talc, mica, titanium dioxide, zinc laurate, zinc myristate, zinc rosinate, alumina, attapulgite, calcium carbonate, calcium silicate, dextran, kaolin, nylon, silica silylate, sericite, soy flour, tin oxide, titanium hydroxide, trimagnesium phosphate, walnut shell powder, or mixtures thereof.

The particulate matter may also include various organic and inorganic pigments. The organic pigments are generally aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes, in particular the Lakes of D&C and FD&C colors. Inorganic pigments include iron oxides, ultramarines, chromium, chromium hydroxide colors, and mixtures thereof. Suitable inorganic pigments include iron oxides.

The above mentioned pigments and particulate fillers may be surface treated with lecithin, amino acids, mineral oil, silicone oil or various other agents either alone or in combination, which coat the particulate surface. The coating used for the surface treatment may be either lipophilic or hydrophilic in character.

Preferably color compositions of the invention will contain both pigments and particulate fillers. Obviously the percentage of pigments used in the particulate phase will depend on the type of cosmetic being formulated. Color cosmetics such as eyeshadow or blush generally have a much higher concentration of color than other types of cosmetics. Generally the weight ratio of pigments to non-pigmented particulates range from 1:50 to 50:1.

B. Antiperspirant Salts

The particulate matter may comprise antiperspirant salts. The term "antiperspirant active salt" or "antiperspirant salt" means any compound or composition having antiperspirant activity, preferably astringent metallic salts such as the inorganic and organic salts of aluminum, zirconium, and zinc, and mixtures thereof. Particularly preferred are the aluminum and zirconium salts such as aluminum halides, aluminum hydroxide halides, zirconyl oxide halides, zirconyl hydroxy halides, and mixtures thereof. Aluminum salts include those of the formula:

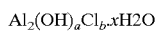

wherein a is from about 2 to 5; a+b=6; x is from about 1 to about 6; and wherein a, b, and x may have non-integer values. Zirconium salts include those of the formula:

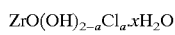

wherein a is from about 1.5 to about 1.87; x is from about 1 to about 7; and wherein a and n may have non-integer values.

Examples of aluminum and zirconium salts include aluminum chloride, aluminumchlorohydrate, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, aluminum zirconium octachlorohdrate, aluminum zirconium octachloroydrex GLY, aluminum zirconium pentachlorohydrate, aluminum zirconium pentachlorohydrex GLY, aluminum zirconium tetrachlorohydrate, aluminum zirconium tetrachlorohydrex GLY, aluminum zirconium trichlorohydrate, aluminum zirconium trichlorohydrex GLY, and mixtures thereof.

Particularly preferred zirconium salts are those complexes also containing aluminum and glycine, in particular, aluminum zirconium tetrachlorohydrex GLY. The antiperspirant salts used in the composition of the invention are solubilized in the water. Preferably the antiperspirant salts present in the claimed antiperspirant compositions are in the crystalline or suspensoid form.

III. Nonpolar Phase

The compositions of the invention comprise 1–70%, preferably 5–65%, more preferably 8–60% by weight of the total composition of a nonpolar phase. The term "nonpolar phase" means at least one nonpolar ingredient which may be in the form of a liquid, solid, or semi-solid. Suitable nonpolar liquids are oils exhibiting a generally lipophilic character, i.e. oils which are miscible or optimally dispersible in other nonpolar ingredients. Suitable nonpolar solids and/or semi-solids include waxes and certain types of synthetic polymers which are lipophilic in character.

A. Nonpolar Oils

The nonpolar oil may be volatile or nonvolatile. The oil may be volatile or non-volatile. The term "volatile" means that the oil has a measureable vapor pressure, or a vapor pressure of at least 2 mm. of mercury at 20° C. The term "nonvolatile" means that the oil has a vapor pressure of less than 2 mm. of mercury at 20° C.

1. Nonpolar Volatile Oils

Suitable nonpolar volatile oils generally have a viscosity of about 0.5 to 10 centipoise at 25° C. Suitable volatile oils include linear silicones, cyclic silicones, paraffinic hydrocarbons, or mixtures thereof.

(a) Volatile Silicones

Cyclic silicones (or cyclomethicones) are of the general formula:

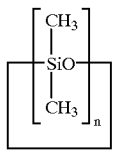

where n=3–7.

Linear volatile silicones in accordance with the invention have the general formula:

where n=0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

(b) Volatile Hydrocarbons

Also suitable as the volatile oils are various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic ydrocarbons are available from EXXON under the ISOPARS trademark, and from the Permethyl Corporation. Suitable $C_{12}$ isoparaffins such as isododecane are manufactured by Permethyl Corporation under the tradename Permethyl 99A. Various $C_{16}$ isoparaffins commercially available, such as isohexadecane (having the tradename Permethyl R), are also suitable. Transfer resistant cosmetic sticks of the invention will generally comprise a mixture of volatile silicones and volatile paraffinic hydrocarbons.

2. Nonpolar Nonvolatile Oils

A wide variety of nonvolatile oils are also suitable for use in the cosmetic compositions of the invention. The nonvolatile oils generally have a viscosity of greater than about 10 centipoise at 25° C., and may range in viscosity up to 1,000,000 centipoise at 25° C. The nonpolar oil may be a variety of silicone or organic natural or synthetic oils.

(a) Esters

Examples of nonvolatile oils suitable for use in the cosmetic sticks of the invention include esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, as well as the esters disclosed on pages 24–26 of the C.T.F.A. Cosmetic Ingredient Handbook, First Edition, 1988, which is hereby incorporated by reference.

(b) Glyceryl Esters of Fatty Acids

The oil may also comprise naturally occuring glyceryl esters of fatty acids, or triglycerides. Both vegetable and animal sources may be used. Examples of such oils include castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

(c) Fatty Acid Glycerides

Also suitable as the oil are synthetic or semi-synthetic glyceryl esters, e.g. fatty acid mono-, di-, and triglycerides which are natural fats or oils that have been modified, for example, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

(d) Nonvolatile Hydrocarbons

Also suitable as the oil are nonvolatile hydrocarbons such as isoparaffins, mineral oil, and so on.

(e) Nonvolatile Silicones

Nonvolatile silicones, both water soluble and water insoluble, are also suitable as the oil component provided they are nonpolar. Such silicones preferably have a viscosity of 10 to 600,000 centipoise, preferably 20 to 100,000 centipoise at 25° C. Suitable water insoluble silicones include dimethicone, amodimethicone, hexadecyl methicone, methicone, phenyl trimethicone, simethicone, dimethylhydrogensiloxane, vinyldimethicone, and mixtures thereof. Also suitable are water soluble silicones such as dimethicone copolyol, provided it is lipophilic and/or nonpolar in character. Such silicones are available from Dow Corning as the 3225C formulation aid, Dow 190 and 193 fluids, or similar products marketed by Goldschmidt under the ABIL tradename.

(f) Nonvolatile Fluorinated Oils

Also suitable as the nonvolatile oil are various fluorinated oils such as fluorinated silicones, fluorinated esters, or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers like those disclosed in U.S. Pat. Nos. 5,183,589, 4,803,067, 5,183,588 all of which are hereby incorporated by reference, which are commercially available from Montefluos under the trademark Fomblin, are also suitable shine enhancers.

(g) Guerbet Esters

Guerbet esters are also suitable oils. The term "guerbet ester" means an ester which is formed by the reaction of a guerbet alcohol having the general formula:

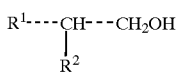

with a carboxylic acid having the general formula:

or

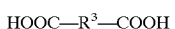

wherein $R^1$ and $R^2$ are each independently a $C_{4-20}$ alkyl and $R^3$ is a substituted or unsubstituted fatty radical such as a $C_{1-50}$ straight or branched chain saturated or unsaturated alkyl or alkylene, or phenyl, wherein the substituents are halogen, hydroxyl, carboxyl, and alkylcarbonylhydroxy. Particularly preferred is a carboxylic acid wherein the R group is such to provide an ingredient known as meadowfoam seed oil.

Preferably, the guerbet ester is a fluoro-guerbet ester which is formed by the reaction of a guerbet alcohol and carboxylic acid (as defined above), and a fluoroalcohol having the following general formula:

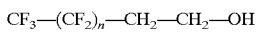

wherein n is from 3 to 40.

Examples of suitable fluoro guerbet esters are set forth in U.S. Pat. No. 5,488,121 which is hereby incorporated by reference. Suitable fluoro-guerbet esters are also set forth in U.S. Pat. No. 5,312,968 which is hereby incorporated by reference. Most preferred is a guerbet ester having the tentative CTFA name fluoro-octyldodecyl meadowfoamate. This ester is sold by Siltech, Norcross Ga. as Developmental Ester L61125A, under the tradename Silube GME-F.

B. Nonpolar Solids and Semi-Solids

1. Waxes

The nonpolar phase may comprise one or more waxy solids. Suitable waxes include animal, plant, mineral, and silicone waxes. Examples of such waxes are apple, avocado, bayberry, beeswax, candelilla, ceresin, cetyl esters, hydrogenated jojoba wax, microcrystalline, hydrolyzed beeswax, jojoba butter, jojoba esters, lanolin, mink, montan, organ, ouricury, oxidized beeswax, ozokerite, palm kernel, paraffin, PEG-beeswax, rice, shellac, polyethylene, and the like. Also suitable are silicone waxes such as stearyl dimethicone, behenoxydimethicone, silicone ester waxes such as those disclosed in U.S. Pat. No. 5,505,937, which is hereby incorporated by reference.

2. Synthetic Polymers

Various synthetic polymers may be suitable for use as the nonpolar phase, provided the synthetic polymers are lipophilic in character. Examples of such synthetic polymers include those made from ethylenically unsaturated monomers, for example, ethylene/propylene copolymers, acrylates, methacrylates, and so on.

IV. Other Ingredients

The compositions of the invention may comprise a number of other ingredients which enhance the beneficial properties thereof, including water sensitive ingredients, humectants, polyols, preservatives, antioxidants, and the like.

A. Water Sensitive Ingredients

The compositions of the invention may comprise 0.1–20%, preferably 0.5–15%, more preferably 1–10% by weight of the total composition of one or more water sensitive ingredients. Suitable water sensitive ingredients include those compounds which are instable when diluted in water, such as ascorbic acid, and derivatives thereof.

The invention will be further described in connection with the following examples which are set forth for the purpose of illustration only.

EXAMPLE 1

An anhydrous ascorbic acid composition was made according to the following formula:

|  | w/w % |
| --- | --- |
| Emulsifying siloxane elastomer[1] | 20.0 |
| Cyclomethicone | 43.0 |
| Ascorbic acid | 4.8 |
| Mica | 0.5 |
| Polymethylmethacrylate | 6.5 |

[1]KSG 21, Shin-Etsu Silicones of America, Akron, Ohio.

The ingredients were mixed well with a Silverson homogenizer at 5000 rpm for about 15 minutes. The result was a smooth, white cream that provided a soft, velvety feel when applied to skin.

EXAMPLE 2

A lipstick composition is prepared as follows:

|  | w/w % |
| --- | --- |
| 1 Candelilla wax | 1.00 |
| 1 Synthetic wax | 9.00 |
| 1 Paraffin | 4.00 |
| 1 Cetyl alcohol | 3.00 |
| 1 C10–30 cholesterol/lanasterol esters | 10.00 |
| 2 Quaternium-18 hectorite | 0.20 |
| 3 Titanium dioxide | 0.95 |
| 3 D & C Red Calcium Lake | 0.60 |
| 3 Mica | 6.00 |
| 3 Iron oxides | 1.00 |
| 3 Trioctyl dodecyl citrate | 7.00 |
| 4 Emulsifying siloxane elastomer* | 3.00 |
| 4 Silicone/acrylate graft copolymer* | 20.00 |
| 4 Isotridecyl isononanoate | 17.125 |
| 4 Trioctyl dodecyl citrate | 17.125 |

*KSG21: Shin-Etsu Silicones of America
*KSG545: Shin-Etsu Silicones of America

Phase 5 is mixed well and heated to 70° C. Separately the Phase 3 ingredients are mixed well and ground with a Silverson homogenizer at a speed of 5000 rpm. All Phases 1–4 are combined and heated to 90° C. for 60 minutes to mix well. The compositions are poured into lipstick molds and allowed to cool.

EXAMPLE 3

A cream blush on composition is made as follows:

|  | w/w % |
| --- | --- |
| 1 Phenyl dimethicone | 12.00 |
| 2 Dimethicone | 10.00 |
| 3 Isostearyl | 8.00 |
| 4 Glyceryl tribehenate | 8.00 |
| 5 Stearyl dimethicone | 5.00 |
| 6 Nylon | 5.00 |
| 7 Talc | 12.00 |
| 8 Polymethylmethacrylate | 3.00 |
| 9 Mineral oil | 3.00 |
| 10 Polyglyceryl 3 diisostearate | 1.50 |
| 11 Phenoxyethanol | 0.50 |
| 12 Methyl paraben | 0.50 |
| 13 Propyl paraben | 0.50 |
| 14 Titanium dioxide | 2.00 |
| 15 Bismuth oxychloride | 5.00 |
| 16 Yellow iron oxide | 1.50 |
| 17 Red iron oxide | 1.50 |
| 18 Black iron oxide | 0.20 |
| 19 D&C Red 7 | 0.80 |
| 20 Ultramarine blue | 1.00 |
| 21 Mica | 5.00 |
| 22 Emulsifying siloxane elastomer* | 15.00 |

*KSG 21 - Shin-Etsu Silicones of America

Ingredients 14–22 are mixed well and ground with a colloid mill. Separately Ingredients 1–13 are mixed well and heated to 90° C. with stirring until a uniform mixture is obtained. Both phases are combined and mixed well. The composition is poured into pans and allowed to cool.

EXAMPLE 4

A powder blush composition is made as follows:

|  | w/w % |
| --- | --- |
| Talc | 35.00 |
| Zinc stearate | 6.00 |
| Kaolin | 12.00 |

-continued

| | w/w % |
|---|---|
| Isopropyl myristate | 5.00 |
| TEA-isostearate | 8.00 |
| Lanolin alcohol | 4.00 |
| Pentahydrosqualene | 2.00 |
| Isostearic hydrolyzed animal protein | 0.50 |
| Methyl paraben | 0.50 |
| Propyl paraben | 0.50 |
| Sodium dehydroacetate | 1.00 |
| Titanium dioxide | 2.00 |
| Bismuth oxychloride | 5.00 |
| Yellow iron oxide | 1.50 |
| Red iron oxide | 0.50 |
| Black iron oxide | 0.20 |
| D&C Red 7 | 0.80 |
| Ultramarine blue | 1.00 |
| Mica | 5.00 |
| Emulsifying siloxane elastomer | 9.50 |

All ingredients except for the siloxane elastomer are mixed well in a blender for 20 minutes. The elastomer is then added to the mixture, and blending continued for an additional 19 minutes. The resulting composition is packed into pans.

EXAMPLE 5

A pressed powder foundation is made according to the following formula:

| | w/w % |
|---|---|
| 1 Talc | 40.00 |
| 2 Polyethylene | 10.00 |
| 3 Silica | 1.00 |
| 4 Zinc stearate | 4.00 |
| 5 Aluminum hydrogenated tallow glutamate | 0.80 |
| 6 Methyl paraben | 0.50 |
| 7 Propyl paraben | 0.50 |
| 8 Titanium dioxide | 10.00 |
| 9 Bismuth oxychloride | 2.00 |
| 10 Yellow iron oxide | 1.50 |
| 11 Red iron oxide | 0.50 |
| 12 Black iron oxide | 0.20 |
| 13 Ultramarine blue | 1.00 |
| 14 Mica | 5.00 |
| 15 Pentahydrosqualene | 2.00 |
| 16 Diisostearyl malate | 0.10 |
| 17 Octyl dimethyl PABA | 4.00 |
| 18 Dimethicone | 2.50 |
| 19 Emulsifying siloxane elastomer | 23.00 |

Ingredients 1–14 are mixed in a blender for 10 minutes. Ingredients 15–19 are then added to the mixture and mixing is continued for an additional 10 minutes. The composition is pressed into pans.

EXAMPLE 6

A concealer composition is made according to the following formula:

| | w/w % |
|---|---|
| 1 Isododecane | 21.0 |
| 2 Isopropyl lanolate | 2.0 |
| 3 Quaternium-18 hectorite | 4.5 |
| 4 Lanolin | 4.0 |
| 5 Castor oil | 8.0 |
| 6 Ceresin | 5.0 |
| 7 Carnauba | 4.0 |
| 8 Lanolin | 3.0 |
| 9 Propylene carbonate | 0.5 |
| 10 Stearalkonium hectorite | 0.5 |
| 11 Beeswax | 2.0 |
| 12 Lanolin alcohol | 1.0 |
| 13 Lanolin acid | 0.5 |
| 14 Methyl paraben | 0.5 |
| 15 Propyl paraben | 0.5 |
| 16 Talc | 12.0 |
| 17 Titanium dioxide | 10.0 |
| 18 Yellow iron oxide | 1.5 |
| 19 Red iron oxide | 0.5 |
| 20 Black iron oxide | 0.2 |
| 21 Ultramarine blue | 1.0 |
| 22 Propylene glycol dicaprylate/dicaprate | 1.0 |
| 23 Emulsifying siloxane elastomer | 17.8 |

Ingredients 17–23 are mixed well and ground in a Silverson homogenizer at 5000 rpm for 10 minutes. Separately, Ingredients 1–16 are mixed well and heated to 90° C. Both phases are then mixed together and ground in the homogenizer at 5000 rpm for 10 minutes.

EXAMPLE 7

An eye shadow stick is made according to the following formula:

| | w/w % |
|---|---|
| 1 Castor oil | 40.0 |
| 2 Octyldodecyl stearoyl stearate | 10.0 |
| 3 Ceresin | 6.0 |
| 4 Caprylic/capric triglyceride | 12.0 |
| 5 Beeswax | 2.0 |
| 6 Candelilla wax | 3.0 |
| 7 Carnauba | 6.0 |
| 8 Quaternium-18 hectorite | 6.0 |
| 9 Methylparaben | 0.5 |
| 10 Propyl paraben | 0.5 |
| 11 Yellow iron oxide | 1.5 |
| 12 Red iron oxide | 0.5 |
| 13 Black iron oxide | 0.2 |
| 14 Ultramarine blue | 1.0 |
| 15 Emulsifying siloxane elastomer | 10.8 |

Ingredients 11–15 are mixed and ground in a Silverson homogenizer at 5000 rpm for 10 minutes. Separately, Ingredients 1–9 are mixed well and heated to 90° C. The two phases are combined and mixed well. The composition is poured into stick molds.

EXAMPLE 8

An anhydrous makeup stick is prepared as follows:

| | w/w % |
|---|---|
| 1 Glyceryl rosinate | 10.0 |
| 2 Isododecane | 50.0 |
| 3 Sodium stearate | 6.0 |
| 4 Butylene glycol | 3.8 |

-continued

| | w/w % |
|---|---|
| 5 Yellow iron oxide | 2.1 |
| 6 Red iron oxide | 0.66 |
| 7 Black iron oxide | 0.13 |
| 8 Titanium dioxide | 8.0 |
| 9 Cyclomethicone | 20.0 |
| 10 Emulsifying siloxane elastomer | 19.31 |

Ingredients 5–10 are mixed and ground in a homogenzier at 5000 rpm for 10 minutes. Separately, Ingredients 1–4 are mixed well and heated to 85° C. The two phases are combined and mixed well. The composition is poured into stick molds and allowed to cool.

EXAMPLE 9

A skin lotion containing vitamin C is made according to the following formula:

| | w/w % |
|---|---|
| 1 Emulsifying siloxane elastomer | 20.0 |
| 1 Cyclomethicone | 43.0 |
| 2 Glycerin | 25.2 |
| 2 Ascorbic acid | 4.8 |
| 2 Mica | 0.5 |
| 2 Polymethylmethacrylate beads | 6.5 |

Phases 1 and 2 are mixed well in a homogenizer for 15 minutes. The composition is poured into jars.

EXAMPLE 10

An antiperspirant stick formula is made as follows:

| | w/w % |
|---|---|
| Cyclomethicone D5 | 39.20 |
| Cyclomethicone D4 | 4.00 |
| Octyldodecanol | 2.00 |
| Hydrogenated polyisobutene | 4.00 |
| Emulsifying siloxane elastomer | 16.0 |
| Stearyl alcohol | 4.5 |
| Hydrogenated castor oil | 0.5 |
| PEG-25 propylene glycol stearate | 0.5 |
| PEG-20 | 0.75 |
| Silica | 0.75 |
| Talc | 0.25 |
| Aluminum zirconium tetrachlorohydrex gly | 25.50 |
| Polyethylene | 0.50 |

The ingredients are mixed well and heated to 80° C. The mixture is poured into stick molds and allowed to cool.

EXAMPLE 11

An antiperspirant gel formula is made as follows:

| | w/w % |
|---|---|
| Cyclomethicone D5 | 24.5 |
| Cyclomethicone D4 | 20.0 |
| Dimethicone 10 | 10.0 |
| Emulsifying siloxane elastomer | 20.0 |
| Al/Zr tetrachlorohydrex gly | 25.5 |

The ingredients are combined and mixed well in a homogenizer at 3000 rpm for 5 minutes. The mixture is poured into containers and allowed to cool.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. An anhydrous cosmetic composition comprising, by weight of the total composition:
   0.1–95% of a polar, emulsifying siloxane elastomer gelling agent,
   0.01–40% particulate material; and
   1–70% of a nonpolar phase comprising a nonpolar oil.

2. The composition of claim 1 wherein the siloxane elastomer is formed by the reaction of a dimethyl methylhydrogen siloxane and a divinyl compound, wherein one or more of the reactants contains hydrophilic groups in sufficient quantity to render the elastomer polar.

3. The composition of claim 1 wherein the emulsifying siloxane elastomer is formed by the addition polymerization of I and II, as defined below:

I. an organohydrogenpolysiloxane as described in A, B, or C wherein:

(A) is $$\frac{R^1_a R^2_b H_c SiO(4-a-b-c)}{2}$$

(1) $R^1$ is a substituted or unsubstituted alkyl, aryl, or aralkyl group having 1–18 carbon atoms, or a halogenated hydrocarbon group; and (2) $R^2$ is $-C_nH_{2n}O(C_2H_4O)_d(C_3H_6O)_eR_3$
   (a) wherein $R^3$ is a hydrogen, a saturated aliphatic hydrocarbon group having 1–10 carbon atoms, or a group $-(CO)-R^5$
      (i) wherein $R^5$ is a saturated aliphatic hydrocarbon having 1 to 5 carbon atoms,
   (b) d is an integer of 2 to 200,
   (c) e is an integer of 0 to 200, provided that d+e is 3–200; and
   (d) n is 2 to 6;

(3) a is 1 to 2.5;
(4) b is 0.001 to 1.0; and
(5) c is 0.001 to 1.0;

(B) is $$\frac{R^1_f H_g SiO(4-f-g)}{2}$$

(1) wherein $R^1$ is the same as defined in formula I(A) above,
(2) f is 1.0 to 3.0;
(3) g is 0.001 to 1.5; and (C) is a mixture of said organohydrogenpolysiloxanes of formulas I(A) and I(B); and II. A compound as described in A, B, or C wherein:
(A) is $C_mH_{2m-1}O(C_2H_4O)_h(C_3H_6O)_iC_mH_{2m-1}$
  (1) wherein h is an integer of 2 to 200,
  (2) i is an integer of 0 to 200 provided that h+i is 3 to 200; and
  (3) m is 2 to 6;
(B) is $$\frac{R^1_j R^4_{k4} SiO(4-j-k)}{2}$$

(1) wherein $R^1$ is the same as defined in formula I(A) above,
  (2) $R^4$ is a monovalent hydrocarbon group having an aliphatic unsaturated bond at the terminal thereof and containing 2 to 10 carbon atoms;
  (3) j is 1.023 to 3.0; and
  (4) k is 0.001 to 1.5;
(C) is a mixture of the polyoxyalkylene of II(A) and the organopolysiloxane of II(B), wherein at least one organohydrogenpolysiloxane of formulas I or at least one polyoxyalkylene of formulas II is contained as an essential component of the addition polymerization.

4. The composition of claim 3 wherein the emulsifying siloxane elastomer is formed by the addition polymerization of I and II wherein I is:
(A)

$$\frac{R^1_a R^2_b H_c SiO(4-a-b-c)}{2}$$

(1) wherein $R^1$ is a substituted or unsubstituted alkyl group having 1–18 carbon atoms; and
  (2) $R^2$ is —$C_nH_{2n}O(C_2H_4O)_d(C_3H_6O)_eR_3$
    (a) wherein $R^3$ is a hydrogen, a saturated aliphatic hydrocarbon group having 1–10 carbon atoms, or a group —(CO)—$R^5$
      (i) wherein $R^5$ is a saturated aliphatic hydrocarbon having 1 to 5 carbon atoms,
    (b) d is an integer of 2 to 200,
    (c) e is an integer of 0 to 200, provided that d+e is 3–200; and
    (d) n is 2 to 6;
  (3) a is 1 to 2.5;
  (4) b is 0.001 to 1.0; and
  (5) c is 0.001 to 1.0.

and wherein II is:
(A) $C_mH_{2m-1}O(C_2H_4O)_h(C_3H_6O)_iC_mH_{2m-1}$
  (1) wherein h is an integer of 2 to 200,
  (2) i is an integer of 0 to 200 provided that h+i is 3 to 200; and
  (3) m is 2 to 6.

5. The composition of claim 1 which is a color cosmetic composition.

6. The composition of claim 5 wherein the particulate material comprises particulates having a particle size of 0.5 to 100 microns.

7. The composition of claim 6 wherein the particulate material is selected from the group consisting of inorganic pigments, organic pigments, non-pigmented powders, and mixtures thereof.

8. The composition of claim 1 which is an antiperspirant.

9. The composition of claim 8 wherein the particulate material comprises antiperspirant salts.

10. The composition of claim 1 wherein the nonpolar phase comprises a liquid oil.

11. The composition of claim 10 wherein the nonpolar phase comprises a liquid oil comprising a volatile oil, a nonvolatile oil, or mixtures thereof.

12. The composition of claim 11 wherein the liquid oil comprises a volatile oil selected from the group consisting of a silicone oil, a paraffinic hydrocarbon, and mixtures thereof.

13. The composition of claim 12 wherein the volatile silicone comprises a cyclic or linear silicone wherein the cyclic silicone has the formula:

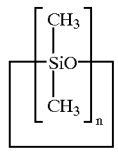

where n=3–6; and the linear silicone has the general formula:

where n=0–15.

14. The composition of claim 1 additionally comprising 0.1–20% by weight of the total composition of a water sensitive agent.

15. The composition of claim 14 wherein the water sensitive agent comprises ascorbic acid.

* * * * *